United States Patent

Rineau

[11] Patent Number: 5,103,834
[45] Date of Patent: Apr. 14, 1992

[54] APPARATUS FOR ORTHOPHONIC DIAGNOSIS AND REEDUCATION

[75] Inventor: Georges Rineau, Nantes, France
[73] Assignee: S.A. Sorefac, Nantes, France
[21] Appl. No.: 513,584
[22] Filed: Apr. 23, 1990

[30] Foreign Application Priority Data

Apr. 26, 1989 [FR] France .............................. 89 05545

[51] Int. Cl.⁵ .............................................. A61B 5/00
[52] U.S. Cl. .................................... 128/724; 128/716; 381/41
[58] Field of Search ............... 128/716, 724, 774, 897; 381/41, 46

[56] References Cited

U.S. PATENT DOCUMENTS

| 3,752,929 | 8/1973 | Fletcher. | |
|---|---|---|---|
| 3,906,936 | 9/1975 | Habal. | |
| 4,377,158 | 3/1983 | Friedman et al. | 128/897 |
| 4,475,559 | 10/1984 | Horn | 128/716 |
| 4,519,399 | 5/1985 | Hori | 128/724 |
| 4,715,367 | 12/1987 | Crossley | 128/774 |
| 4,777,963 | 10/1988 | McKenna | 128/724 |

Primary Examiner—Lee S. Cohen
Assistant Examiner—K. M. Pfaffle
Attorney, Agent, or Firm—Young & Thompson

[57] ABSTRACT

An apparatus for the detection of malformations and for orthophonic reeducation by visual control of nasal breathing and of speech sounds in a human subject. A housing has two conduits so spaced and oriented as to be adapted to be brought into juxtaposition with the nostrils of a human subject. A thermistor is disposed in each conduit. A microphone is so disposed in the housing as to face the mouth of a human subject when the conduits are juxtaposed with the nostrils of the same human subject. Signals from said thermistors and the amplitude of sounds received by the microphone are measured and separately displayed.

6 Claims, 1 Drawing Sheet

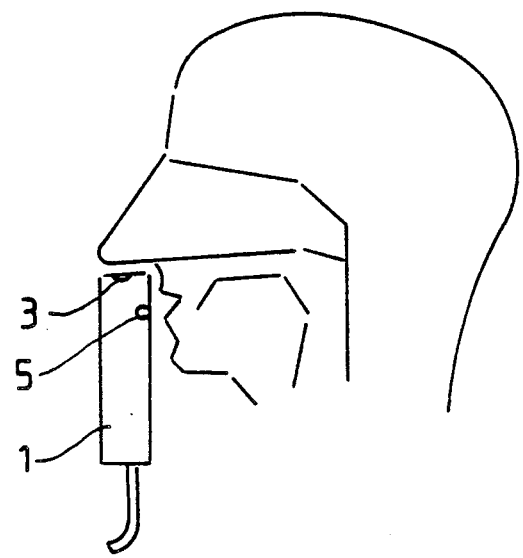
FIG.1
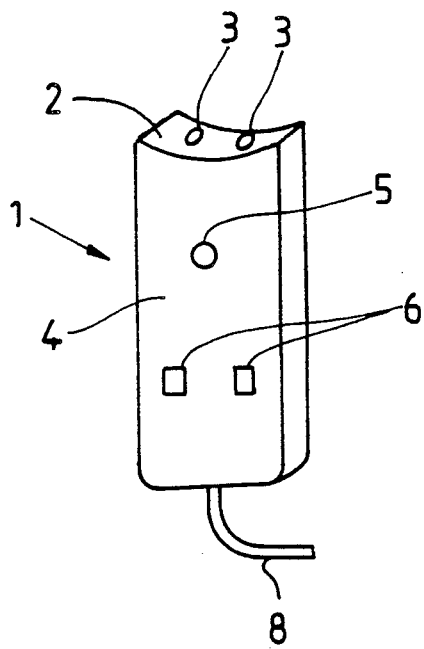
FIG.2
FIG.3
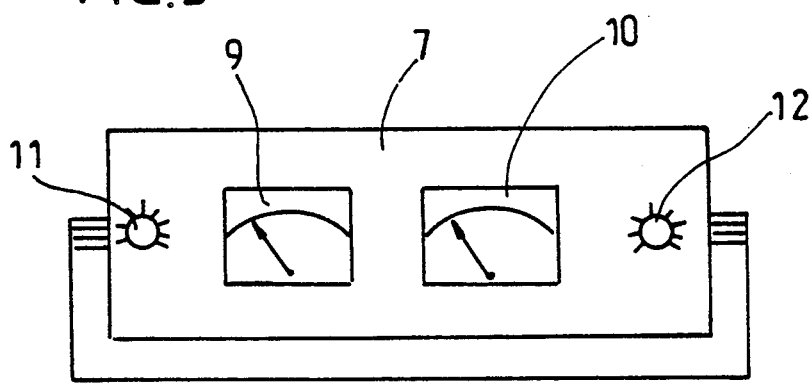

APPARATUS FOR ORTHOPHONIC DIAGNOSIS AND REEDUCATION

FIELD OF THE INVENTION

The invention relates to an apparatus for orthophonic diagnosis and reeducation by visual control of the nasal breathing and the emission of vocal sounds, of the type comprising a sensor of nasal breath and a buccal sensor, as well as, means for displaying the values measured by said sensors.

DESCRIPTION OF THE RELATED ART

There have been proposed many processes and apparatuses to measure nasal breathing, essentially with the aim of determining the presence of insufficiencies or clefts at the level of the pallet or of the nasal partition.

It has thus been proposed (see the introduction of FR-A-2,537,429) to detect vibrations of the nasal partition and, simultaneously, the acoustic waves emitted from the patient's mouth, and to compare the signals thus emitted. This known procedure does not permit measuring with certainty the degree of nasality in all cases, particularly in the case of a slightly cleft pallet. Moreover, the detection of vibrations of the nasal partition is thrown off by the distance between the detector and the partition, such that the result is inexact.

FR-A-2,537,429, to eliminate these defects, proposes to measure the air flows exhaled respectively by the nose and by the mouth. To do this, a combined mask for the nose and the mouth must be applied to the face with a sealing separation between the two organs. It will be recognized that such an apparatus, whose results are in any event questionable, cannot be used for an infant of tender age although it is in babies that the detection of insufficiencies must be the most often effected. Moreover, such a mask cannot be used for reeducation because it cannot be worn very long by a patient.

Such a mask has been proposed in U.S. Pat. No. 3,752,929, the analysis being effected by two microphones, one for the nose and one for the mouth. In addition to the preceding drawbacks, the partitions separating the two microphones cannot let sounds pass. Such a condition is practically impossible.

In U.S. Pat. No. 3,906,936, it has been proposed to measure the flow of nasal air by means of a thermistor mounted in a mask and more or less cooled by the emitted flow of air. This known measurement procedure has the same drawbacks as those previously indicated.

SUMMARY OF THE INVENTION

The present invention accordingly aims to provide an apparatus of the type described in the introduction which permits rapid and certain detection of the nasal breathing during speech, at the precise moments of vocal emissions and outside the breathing times, without disturbing the observation of nasal breathing by respiratory breathing, and which permit prolonged use, if desired autonomously, for reeducation.

To this end, the process of using the inventive apparatus is characterized by the fact that there is placed before each nostril a conduit provided with a thermistor, there is placed before the mouth a microphone, and the values read by the thermistors and by the microphone are separately analogically displayed.

Because the analysis of nasal breathing is effected by a procedure different from that used for the analysis of buccal breathing, there is no interference between the values read and displayed. The instantaneous display in analogic form permits the operator to perform an immediate diagnosis by the pronunciation of certain test sounds and permits the patient to recognize his own defects and correct them.

The apparatus according to the invention is characterized by the fact that it comprises a support or housing provided with two conduits whose outlet opens toward each of the respective nostrils, and a microphone placed before the mouth, each conduit being provided with a thermistor, the apparatus comprising moreover means for measuring and displaying the current flowing from the thermistors and means to measure and display the amplitude of the sounds received by the microphone.

Preferably, the apparatus comprises means for selectively indicating values read by one or the other of the thermistors, so as to verify individually the breath emitted by each nostril. These selective elimination means may comprise a switch for cutting out the thermistor.

According to one embodiment of the invention, the apparatus comprises moreover stereophonic and/or graphic sound recordation means for the measured values.

The apparatus according to the invention, which is more a comparison device than a precise measuring device, permits translating into arbitrary terms on a screen or viewer the presence or absence of nasal breath during speech which is simultaneously analyzed to ensure control. The apparatus permits effecting these measures for both nostrils simultaneously or for each nostril separately. The intensity of laryngeal or whispered oral emission being reproduced simultaneously on a display or viewer, the patient and/or the user can establish a comparative study between the nasal breathing and the oral emission.

The use of a common support for the nasal conduits and the microphone permits prolonged utilization for reeducation, this support being simply placed in front of the face.

The apparatus may also comprise a second support identical to the first and used by the instructor.

DESCRIPTION OF THE DRAWINGS

The invention will be better understood from the reading of the following description given with reference to the accompanying drawing in which:

FIG. 1 is a schematic view of a support of an apparatus according to an embodiment of the invention, in use position;

FIG. 2 is a schematic view in perspective on a larger scale of the support of FIG. 1; and FIG. 3 is a schematic plan view of a console of the apparatus.

DETAILED DESCRIPTION OF THE INVENTION

The apparatus comprises a support or housing 1 comprising on a smaller surface 2, which is slightly concave, the ends 3 of two conduits. On a larger surface 4, the housing 1 comprises a piezoelectric microphone 5 and two switches 6. The arrangement is such that, as shown in FIG. 1, the ends 3 of the conduits may be disposed respectively below each nostril of a person, the microphone 5 being simultaneously in front of the mouth.

The conduits terminating at the ends 3 each contain a resistant wire or thermistor fed with direct current and a measurement circuit of the voltage at the terminals of the wire. This voltage varies with the temperature of the wire, which is modified by the air flow leaving the adjacent nostril. The measured voltage is therefore a function of nasal breathing.

The housing 1 is connected to a console 7 of the apparatus (FIG. 3) by a cable 8. The cable 8 contains the feed wires of the thermistors and of the microphone 5, from an electrical source or a transformer or rectifier contained in the console 7. The measurement circuit and the microphone 5 are connected to an electronic apparatus also contained in the console 7 and which controls a meter 9 with analogic display of the nasal breathing measured by the thermistors and a meter 10 with analogic display of the amplitude of speech, after rectification. The buttons 11 and 12 permit regulating respectively the sensitivity of the meters 9 and 10. The switches 6 serve respectively to cut out one or the other of the thermistors.

The console 7 may comprise an input for a second housing 1, an output for stereophonic sound recordation, and an output for a graphic recordation.

The apparatus comprises also a sound signal emitter which is triggered in precise synchronization with the movement of the nasal meter needle to signal to the person to be reeducated the presence of nasal emission during reading out loud.

The apparatus which has been described permits detecting certain anomalies such as open or closed rhinolalies, velar insufficiencies, nasality, nasal obstructions, or uncontrolled emissions during deafness. It also permits educating or reeducating these same phonetic difficulties.

There can be provided in the course of reeducation, audition means disposed within a helmet or the like, of the emission spoken by the tested subject and sensed by the microphone, when this emission is stripped of all nasality.

It is also possible to include a recordation of the laryngeal vibrations by means of a sensor disposed on the thyroid cartilage and to display it on a calibrated intensity scale, so as to display the detection of the malformations.

I claim:

1. Apparatus for the detection of malformations and orthophonic reeducation by visual control of nasal breathing and of speech sounds, comprising a housing having two conduits so spaced and oriented as to be adapted to be brought into juxtaposition with the nostrils of a human subject, thermistor means in each of said conduits for sensing temperatures of said nasal breathing and for generating signals representative of said sensed temperatures, a microphone so disposed in the housing as to face the mouth of said human subject when said conduits are juxtaposed with the nostrils of the same human subject for receiving speech sounds, means for measuring said generated signals from said thermistor means and the amplitude of sounds received by the microphone, and means for separately displaying said measurements; said housing having two adjacent sides disposed at a substantial angle to each other, said conduits being disposed in one of said two sides and said microphone being disposed in the other of said two sides.

2. Apparatus as claimed in claim 1, said display means comprising a pair of immediately adjacent meters, one of which displays said measurements from said thermistor means, and the other displays said measurements from said microphone.

3. Apparatus as claimed in claim 1, further comprising means for adjusting the sensitivity of said measurements.

4. Apparatus for the detection of malformations and orthophonic reeducation by visual control of nasal breathing and of speech sounds, comprising a housing having two conduits so spaced and oriented as to be adapted to be brought into juxtaposition with the nostrils of a human subject, thermistor means in each of said conduits for sensing temperatures of said nasal breathing and for generating signals representative of said sensed temperatures, a microphone so disposed in the housing as to face the mouth of said human subject when said conduits are juxtaposed with the nostrils of the same human subject for receiving speech sounds, means for measuring said generated signals from said thermistor means and the amplitude of sounds received by the microphone, means for separately displaying said measurements; and means for selectively eliminating signals generated by one of the thermistor means.

5. Apparatus as claimed in claim 4, said display means comprising a pair of immediately adjacent meters, one of which displays said measurements from said thermistor means, and the other displays said measurements from said microphone.

6. Apparatus as claimed in claim 4, further comprising means for adjusting the sensitivity of said measurements.

* * * * *